United States Patent [19]

Kano

[11] Patent Number: 4,835,274
[45] Date of Patent: May 30, 1989

[54] LIQUID CRYSTAL COMPOUND

[75] Inventor: Mitsuru Kano, Furukawa, Japan

[73] Assignee: Alps Electric Co., Ltd., Japan

[21] Appl. No.: 17,473

[22] Filed: Feb. 20, 1987

[30] Foreign Application Priority Data

Jun. 13, 1986 [JP] Japan ................ 61-137788

[51] Int. Cl.$^4$ .................. G02F 1/13; C09K 19/34; C07D 237/00; C07D 237/02; C07D 239/02

[52] U.S. Cl. ............... 544/239; 252/299.01; 252/299.5; 252/299.61; 350/350 R; 350/350 S; 544/224; 544/248; 544/318; 544/335; 544/336; 544/408

[58] Field of Search ......... 252/299.01, 299.5, 299.61; 350/350 R, 350 S; 544/224, 239, 318, 335, 298, 408, 336

[56] References Cited

U.S. PATENT DOCUMENTS

| | | | |
|---|---|---|---|
| 4,011,610 | 1/1982 | Zaschk et al. | 252/299.61 |
| 4,623,477 | 11/1986 | Ogawa et al. | 252/299.61 |
| 4,657,695 | 4/1987 | Saito et al. | 252/299.61 |
| 4,709,030 | 11/1987 | Petzilka et al. | 252/299.61 |
| 4,713,197 | 12/1987 | Eidenschink et al. | 252/299.61 |
| 4,721,367 | 1/1988 | Yoshinaga et al. | 252/299.61 |

FOREIGN PATENT DOCUMENTS

| | | |
|---|---|---|
| 149238 | 7/1985 | European Pat. Off. ........ 252/299.61 |
| 3404117 | 8/1985 | Fed. Rep. of Germany ........ 252/299.61 |
| 3515073 | 11/1986 | Fed. Rep. of Germany ........ 252/299.61 |
| 3518704 | 11/1986 | Fed. Rep. of Germany ........ 252/299.61 |
| 3600052 | 7/1987 | Fed. Rep. of Germany ........ 252/299.61 |
| 60-92276 | 5/1985 | Japan ........ 252/299.61 |
| 61-215375 | 9/1986 | Japan ........ 252/299.61 |
| 62-71 | 1/1987 | Japan ........ 252/299.61 |
| 2092169 | 8/1982 | United Kingdom ........ 252/299.61 |
| 86/00067 | 1/1986 | World Int. Prop. O. ........ 252/299.61 |
| 86/00087 | 1/1986 | World Int. Prop. O. ........ 252/299.61 |

OTHER PUBLICATIONS

Zaschke, H. et al., J. Prakt. Chem., vol. 321(4), pp. 619-628 (1979).
Isenberg, A. et al., Z. Chem., vol. 23(8), pp. 296-297 (1983).
C.A. 92:58715c (1980).
Demus, D. et al., Flüssige Kristalle in Tabellen II, VEB Deutscher Verlag fur Grundstoffindustrie, Leipzig, pp. 372-388 (1984).
Zaschke, H., Advances in Liquid Crystal Research and Applications, Bata, L., Pergamon Press, Oxford, pp. 1059-1074 (1980).
Gray, G. W. et al., Liquid Crystals & Plastic Crystals, vol. 1, John Wiley & Sons, Inc., N.Y., pp. 142-143 (1974).

Primary Examiner—Teddy S. Gron
Attorney, Agent, or Firm—Guy W. Shoup; Paul J. Winters; Stephen L. Malaska

[57] ABSTRACT

A liquid crystal compound comprising the following general formula (1):

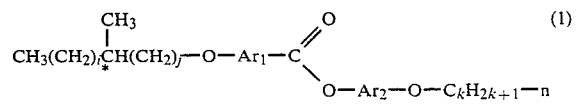

where i, j and k individually represent an integer within a range: $1 \leq i \leq 8$, $0 \leq j \leq 7$, $4 \leq k \leq 14$, $Ar_1$ represents

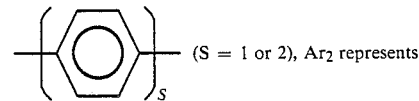

(S = 1 or 2), $Ar_2$ represents

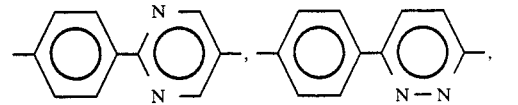

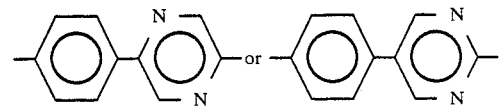

*represents an asymmetric carbon and the compound is required to be optically active. The compound can provide various merits as the chiral substance such as satisfactory optical rotation, capability of inducing twisted arrangement when added to the TN system or phase transition system liquid crystal mixture, and of enlarging the liquid crystal temperature range when added to SmC* liquid crystal mixture.

1 Claim, No Drawings

LIQUID CRYSTAL COMPOUND

BACKGROUND OF THE INVENTION

1. Field of the Invention

This invention concerns a liquid crystal compound for use in liquid crystal devices and, particularly, it relates to a novel optically active (chiral) substance inducing twisted arrangement in liquid crystals.

2. Description of the Prior Art

As the operation principle for liquid crystal display devices, there have been known a twisted nematic (TN) system using a nematic liquid crystal phase, a phase transition system using a cholesteric liquid crystal phase and the like. In any of these systems, liquid crystal mixtures in which chiral substances are added with an aim of inducing the twisted arrangement in the liquid crystals have been used. Further, an attention has been attracted to a high speed light switching device by using smectic liquid crystals, particularly, a smectic C* (SmC*) liquid crystal phase having a feature in the twisted arrangement and utilizing the ferroelectric property thereof in recent years. In this device, a SmC* liquid crystal compound which is a chiral substance per se or a SmC* liquid crystal mixture incorporated with chiral substance have been used.

In this way, the chiral substance inducing the twisted arrangement is extremely important for liquid crystal display devices. However, it is necessary for the chiral substances used in liquid crystal display devices or the likes that not only they have rotatory power but it is also important that the substances per se are of liquid crystal property or the liquid crystal property is not reduced remarkable when they are added to the liquid crystal mixture. Any way, it is important that the liquid crystal property of the liquid crystal mixture is not lost when the substances added thereto.

However, there have been only few chiral substances that can completely satisfy the demands as described above.

OBJECT OF THE INVENTION

Accordingly, it is an object of this invention to provide a novel liquid crystal compound capable of satisfying the demands for the chiral substance in view of the foregoing problems in the prior art.

SUMMARY OF THE INVENTION

The present inventors have made an earnest study for attaining the foregoing purpose and, as a result, have accomplished this invention based on the finding that the liquid crystal compound represented by the following general formula (1) has excellent characteristics as the chiral substance.

That is, the present invention relates to a liquid crystal compound represented by the following general formula (1):

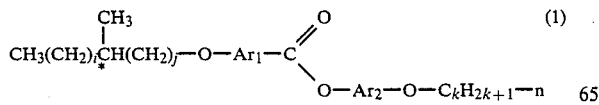

were i, j and k represent an integer in which $1 \leq i \leq 8$, $0 \leq j \leq 7$, $4 \leq k \leq 14$. $Ar_1$ represents

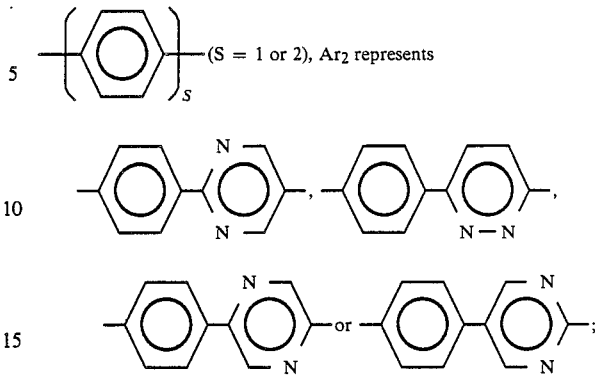

further, * represents asymmetric carbon and the compound is required to be optically active.

The compound represented by the general formula (1) has features in that (a) the main skelton has an ester structure as the liquid crystal skelton (b) $Ar_2$ skelton such as of phenyl pyrimidine with an extremely high liquid crystal property is present in the structure of the main skelton, (c) an asymmetric carbon represented by the symbol * and developing the rotatory power is arranged to one of the end groups, (a) and (b) are structures generally found in liquid crystal compounds and are important for the liquid crystal property. Further, (c) is important for the optical activity. In view of the above, it can be seen that the compound represented by the following formula (1) has satisfactory structure for the demands to the chiral substance.

The compound according to this invention represented by the general formula (1) as described above can be synthesized, for example, in accordance with the synthesis route as described below.

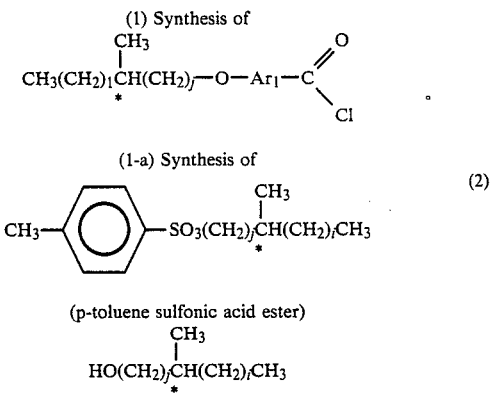

and commercially available p-toluene sulfonic chloride are reacted in equal molar ratio under the presence of pyridine at a low temperature. By extracting the reaction product with benzene under an acidic condition with hydrochloric acid, washing and then distilling off benzene, aimed product can be obtained.

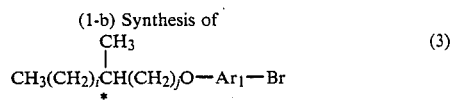

The compound (2) synthesized in (1-a) and commercially available HO—Ar$_1$—Br and potassium hydroxide are reacted by an equivalent molar ratio in an ethanol solvent under heating. The aimed product can be obtained by distilling off ethanol, dissolving the product into benzene and then washing with acid, alkali and water, distilling off benzene and applying vacuum distillation.

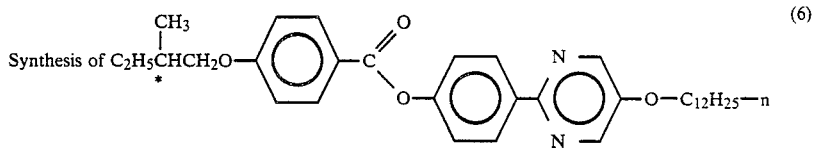

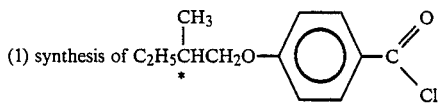

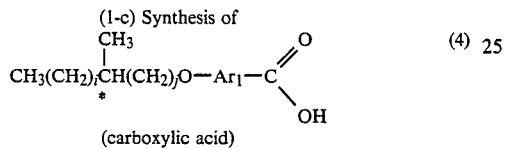

(carboxylic acid)

A Grignard reagent is prepared in accordance with an ordinary method from the compound (3) synthesized in (1-b) and metal magnesium. The reaction is preferably carried out in anhydrous tetrahydrofuran (THF). Then, gaseous carbon dioxide is introduced under a low temperature followed by hydrolysis. The aimed product can be obtained by collecting the reaction product by filtration and recrystallizing from ethanol.

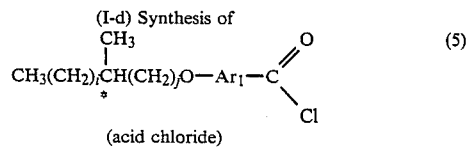

(acid chloride)

The compound (4) synthesized in (1-c) and about three molar times of thionyl chloride (SOCl$_2$) are reacted under heating. By distilling off excess SOCl$_2$ and purifying the product under vacuum distillation, the aimed product (5) can be obtained.

(2) Synthesis of the compound represented by the general formula (1)

The compound can be synthesized referring to the known method (for instance, H. Zaschke, Z. Chem 17. Jg. (1977) Heft 9, or H. Zaschke, Journal f. prukt. Chemie, Band 317, Heft 4, 1975, S. 617). Alternatively, commercially available HO—Ar$_2$—O—C$_k$H$_{2k+1}$—n and an equimolar amount of the compound (5) are reacted in the presence of pyridine in toluene under heating. The aimed product can be obtained by washing the reaction product with acid, alkali and water, distilling off toluene and then recrystallizing from ethanol.

The compound represented by the general formula (1) according to this invention thus synthesized can satisfy the demands for the chiral substance. Accordingly, it can be utilized for the liquid crystal mixture constituting the liquid crystal display device of TN system and phase transition system. Further it can also be utilized for SmC* liquid crystal mixture.

DESCRIPTION OF PREFERRED EMBODIMENTS OF THE INVENTION

Example 1

20.8 g of commercially available active amyl alcohol

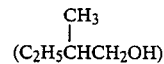

45 g of p-toluene sulfonic chloride and 75 g of pyridine were mixed and brought into reaction for about 8 hours while maintaining the reaction temperature to less than 20° C. Then, 250 ml of 2N-hydrochloric acid were added thereto and benzene was further added to extract the aimed product into the benzene layer. After washing the benzene layer with saturated saline water and with water, benzene was distilled off to obtain p-toluene sulfonic acid ester. The yield was 55 g. Then, 30.5 g of the thus obtained product, 21.8 g of commercially available p-bromophenol and 7.8 g of potassium hydroxide were reacted under heating for 48 hours in 250 ml of ethanol. After distilling off ethanol, the product was dissolved in 250 ml of benzene and then washed with each 250 ml of 6N-hydrochloric acid, 2N-sodium hydroxide and purified water respectively each by three times and then benzene was distilled off. Then, the product was purified under vacuum distillation. The yield was 20 g. Then, 20 g of the synthesized product and 2 g of metal magnesium were charged in a reaction vessel thoroughly dried with phosphor pentoxide and a Grignard reagent was prepared by adding a small amount of I$_2$ in THF solvent. Gaseous carbonic dioxide was introduced while cooling the reagent to less than 0° C., then 500 ml of 2N sulfuric acid were added and stirred under heating at 80° C. for about 2 hours. Then, they were stirred at a room temperature for about 4 hours and the deposited crystals were collected by filtration. The thus obtained crystals were recrystallized from ethanol. As a result, 13 g of carboxylic acid were obtained. Then, 13 g of carboxylic acid and 20 g of thionyl chloride were reacted under heating for about 2 hours. Then, excess thionyl chloride were distilled off from the reaction solution and the aimed product was obtained by distilling the reaction product under vacuum. The yield was 14 g.

(2) Synthesis of the compound represented by the general formula (6)

4.0 g of commercially available

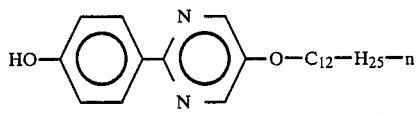

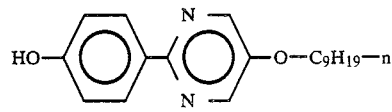

and 2.6 g of the acid chloride obtained in (1) above were stirred together with 2.7 g of pyridine in 250 ml of toluene under heating for about 24 hours. Then, the reaction solution was poured into 500 ml of water to extract the aimed product into the toluene layer and, after washing with each 500 ml of 6N-hydrochloric acid, 2N-sodium hydroxide and purified water each by three times respectively, toluene was distilled off. The product was recrystallized three times from ethanol to obtain an aimed product. The yield was 5.4 g. The thus obtained compound was confirmed to be the compound represented by the compound (6) as described above from the result of IR, $^{13}C$-NMR and liquid chromatography. The phase transition of the compound is:

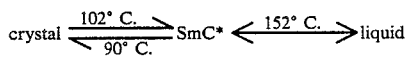

The optical rotation $(\alpha)_D^{26} = +4.0°$

When the compound was added by 1% in weight ratio to 100% of a commercially available biphenyl type liquid crystal mixture and poured into a liquid crystal display cell of TN system, a liquid crystal display device showing satisfactory operation could be obtained. Further, when the compound was added by 2-3% in weight ratio to 100% of the similar liquid crystal compound and then poured into a liquid crystal display device cell, liquid crystal display device of a White Tailor type phase transition system could be obtained.

Examples 2, 3

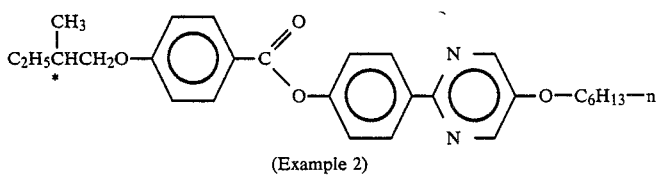

(Example 2)

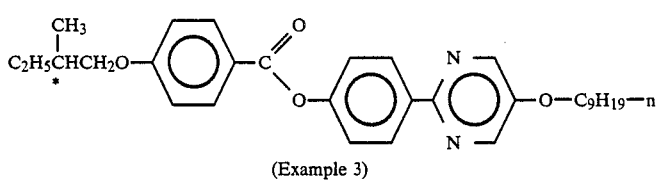

(Example 3)

were synthesized in accordance with the same procedures as in Example 1 excepting for using

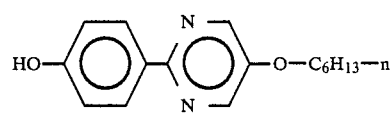

(Example 2) and (Example 3) instead of used in Example 1 (2). The phase transition and optical rotation $(-\alpha)_D^{26}$ of these compounds were as below:

Compound (7)

crystal ⇌ 110° C. / 98° C. SmC* ⇌ 130° C. liquid $(\alpha)_D^{26} = +4.3°$

Compound (8)

crystal ⇌ 107° C. / 95° C. SmC* ⇌ 145° C. liquid $(\alpha)_D^{26} = +4.1°$

When the compound were added to the similar liquid crystal mixture to that in Example 1, a similar liquid crystal display device could be obtained.

Example 4

Similar effects could be obtained by not directly using the active amyl alcohol

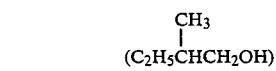

used in Example 1 (1) but by using optically active alcohol

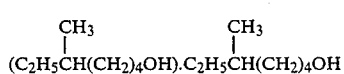

was synthesized as below. At first, 500 g of phosphor tribromide and 100 g of pyridine were added to 300 g of the active amyl alcohol and reacted under ice cooling. Then, the product was distilled moderately under a reduced pressure at 300 mmHg, the fraction was dissolved in petroleum ether, sufficiently washed with 5% sodium hydroxide, 10% sulfuric acid, concentrated sulfuric acid and then purified water, the petroleum ether was distilled off and atmospheric distillation was applied to obtain 300 g of bromide. The same Grignard reagent as in Example 1 was prepared from 130 g of the bromide and 21 g of metal magnesium. 50 g of trimethylene oxide were added to the reagent, hydrolized with 2N-sulfuric acid, extracted with diethylether and, after distillation of ether, the aimed product was obtained through vacuum distillation. The yield was 20 g.

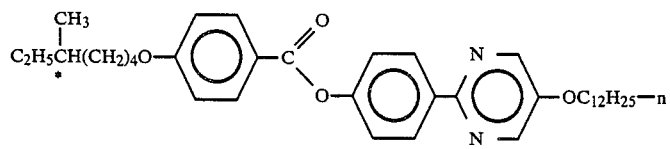

was synthesized in the same procedures as in Example 1 by using the thus obtained product. The phase transition and $(\alpha)_D^{26}$ of the compound was:

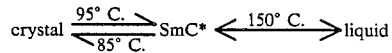

$(\alpha)_D^{26} = +2.5°$

When the compound was added to the similar liquid crystal mixture with that in Example 1, a similar liquid crystal device could be obtained.

Examples 5, 6, 7, 8

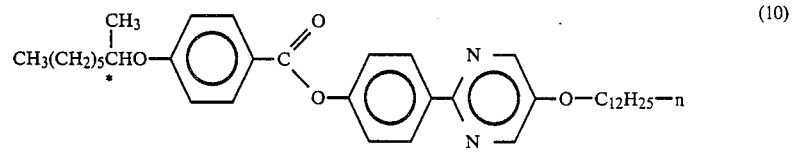

(Example 5)

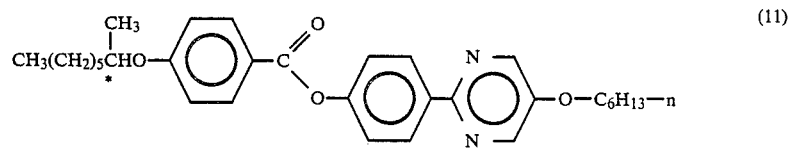

(Example 6)

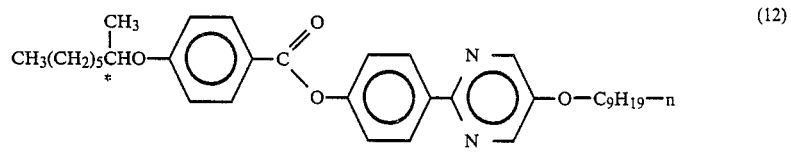

(Example 7)

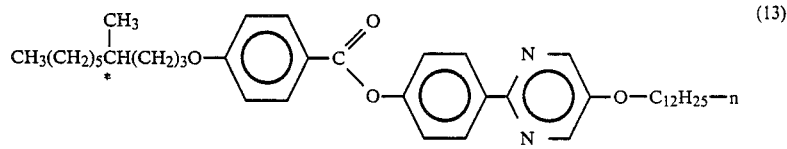

(Example 8)

were synthesized by the same procedures as in Examples 1-4 excepting for using (+)-2-octanol instead of the synthesized product from the active amyl alcohol in Examples 1-4 (1). These compounds showed liquid crystal properties equivalent to those of Examples 1-4 respectively and when they were added to the similar liquid crystal mixture as in Example 1, similar liquid crystal display devices could be obtained.

Examples 9, 10

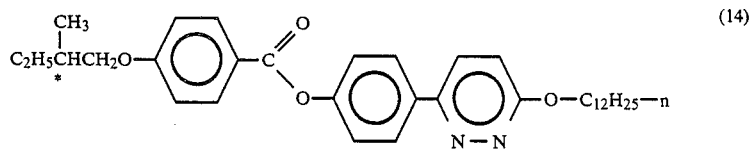

(Example 9)

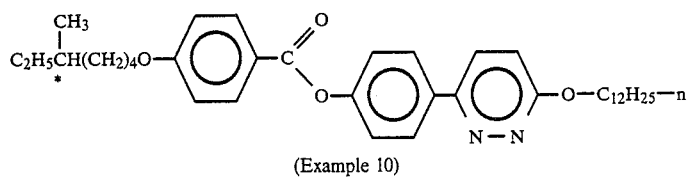

(Example 10)

were synthesized according to the similar procedures by using

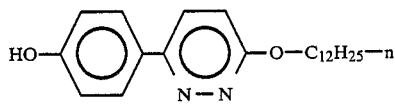

synthesized referring to H. Zaschke, Z. Chem. 17. Jg. (1977) Heft 9 instead of

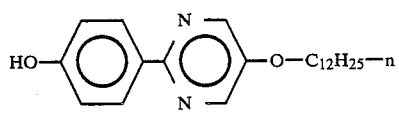

used in Examples 1-4 (2). These compounds showed liquid crystal properties equivalent to those of Examples 1-4 respectively and when they were added to the same liquid crystal compound as in Example 1, the similar liquid crystal devices could be obtained.

Example 11

SmC* liquid crystal compositions as prepared by using known SmC* liquid crystal compounds (16) and (17).

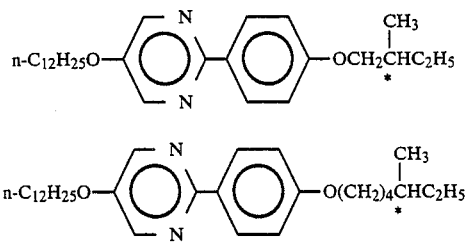

The phase transition of SmC* liquid crystal composition comprising compound (16):compound (17)=30:70 (weight ratio) was:

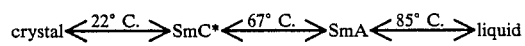

When the compound (6) in Example 1 was added by 30% to the liquid crystal composition, since the temperature range for the SmC liquid crystal phase can be improved being extended as 10° C.-72° C., it can be said as an extremely useful compound. Similar effects can also be found in those compounds prepared from Examples 2-10.

As has been described above, since the compound represented by the general formula (1) is provided according to this invention and the compound itself has liquid crystal property and satisfactory optical rotation, excellent chiral liquid crystal compound can be provided.

Accordingly, the compound according to this invention can be added to a TN system liquid crystal mixture or a phase transition system liquid crystal mixture to induce the twisted arrangement. Further, it can also be added to a SmC* liquid crystal mixture to extend and improve the temperature range for liquid crystals.

What is claimed is:

1. A liquid crystal compound comprising the following general formula (1):

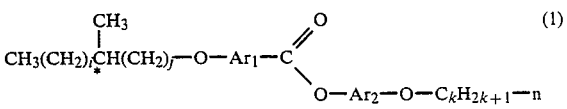

where i, j and k individually represent an integer within a range: $1 \leq i \leq 5$, $0 \leq j \leq 4$, $6 \leq k \leq 12$, $Ar_1$ represents

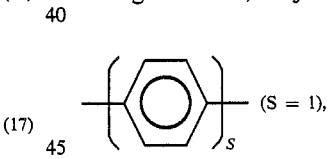

$Ar_2$ represents a 1,4-phenylene ring system of

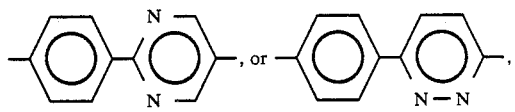

* represents an asymmetric carbon and the compound is required to be optically active.

* * * * *